Figure 1A:
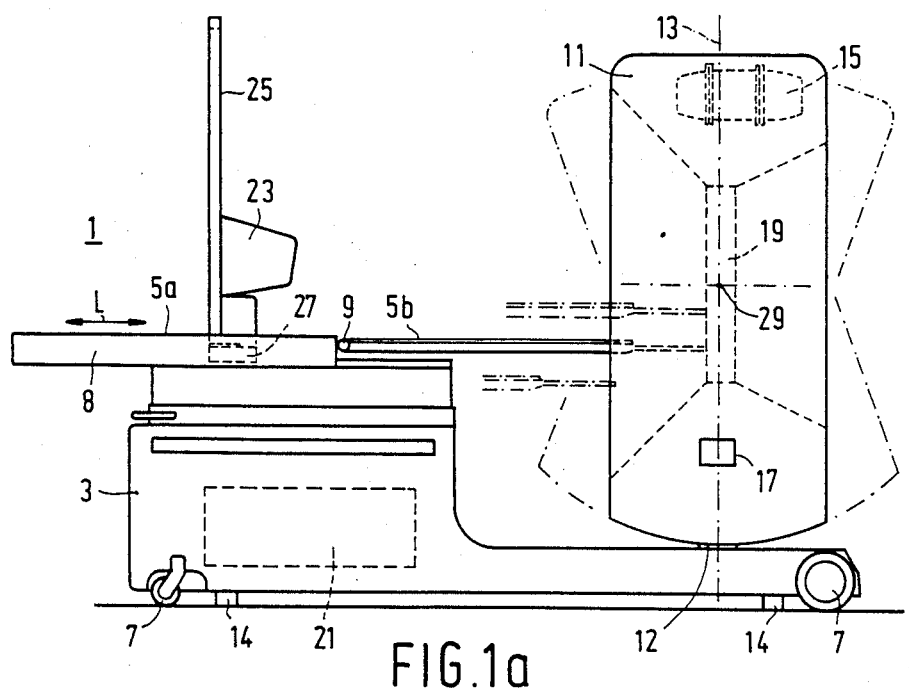

United States Patent [19]

Van der Ende

[11] Patent Number: 4,977,588
[45] Date of Patent: Dec. 11, 1990

[54] X-RAY EXAMINATION APPARATUS

[75] Inventor: Adrianus Van der Ende, Eindhoven, Netherlands

[73] Assignee: U.S. Philips Corporation, New York, N.Y.

[21] Appl. No.: 493,032

[22] Filed: Mar. 12, 1990

[30] Foreign Application Priority Data

Mar. 16, 1989 [NL] Netherlands .................. 8900638

[51] Int. Cl.⁵ .................. A61B 6/00; H05G 1/02
[52] U.S. Cl. .................. 378/196; 378/4; 378/20; 378/17; 378/195; 378/198; 378/197
[58] Field of Search .......... 378/20, 196, 208, 209, 378/17, 195, 197, 198, 4

[56] References Cited

U.S. PATENT DOCUMENTS

| | | | |
|---|---|---|---|
| 3,803,417 | 4/1974 | Kok | 378/196 |
| 4,343,996 | 8/1982 | Kuipers | 378/4 |
| 4,455,667 | 6/1984 | Schwierz et al. | 378/4 |
| 4,872,187 | 10/1989 | Nakahata et al. | 378/4 |

FOREIGN PATENT DOCUMENTS

| | | |
|---|---|---|
| 0297138 | 1/1987 | European Pat. Off. . |
| 3321057 | 6/1983 | Fed. Rep. of Germany . |
| 1269786 | 12/1961 | France . |

Primary Examiner—Janice A. Howell
Assistant Examiner—Kim-Kwok Chu
Attorney, Agent, or Firm—William Squire

[57] ABSTRACT

An X-ray examination apparatus comprises a mobile base on which a table top is also mounted. An X-ray source and detector are secured to the base on a pivotal support. For transporting the X-ray examination apparatus, the support is rotated through 90° with respect to the base, so that the overall width of the apparatus does not exceed the wheelbase of the base. A radiation shielding control console is secured to the wheelbase base so that it can be swung aside.

10 Claims, 2 Drawing Sheets

X-RAY EXAMINATION APPARATUS

The invention relates to an X-ray examination apparatus comprising a patient table with a mobile base and a supporting means whereto an X-ray source and an array of X-ray detectors are connected, which X-ray source is rotatable in a trajectory plane around an object to be arranged on the patient table, during which rotation a substantially flat slice of the object can be irradiated from different directions, X-rays attenuated by the object being detectable by the detectors and an absorption distribution of the slice can be determined from detector signals.

An X-ray examination apparatus of this kind is known from U.S. Pat. No. 4,343,996.

The cited Specification describes an X-ray examination apparatus, notably a computer tomography apparatus, in which the X-ray source and the X-ray detector are rotatable together along a circular path around a common axis of rotation. An object to be examined, for example a patient, can be arranged on the patient table within the circular path. By irradiating the object from a number of positions situated on the circular path, the absorption distribution in the plane in which irradiation directions are situated can be construed from the detector signals by a computer device. The X-ray examination apparatus and the patient table are rigidly connected to a foundation. As a result, an examination room in which the apparatus is erected often can no longer be used for purposes other than examinations by means of the apparatus. Furthermore, the examination room necessitates special measures to be taken in respect of radiation shielding.

It is an object of the invention to provide an X-ray examination apparatus whose use is not restricted to a given location and which does not necessitate the use of special local radiation shielding means.

To achieve this, an X-ray examination apparatus in accordance with the invention is characterized in that the supporting means is arranged on the base and can be swivelled with respect to the base around a swivel axis extending perpendicularly to the base.

Because the supporting member can be swivelled, the trajectory plane can be positioned parallel to the longitudinal direction of the base. The combination of the X-ray apparatus and the base thus constitutes a mobile unit which can be readily displaced without colliding with door posts and which fits in comparatively small spaces such as elevators. When the X-ray apparatus is not in use in the examination room, it can be moved against a wall of the examination room in a compact condition, so that the examination room becomes available for other purposes. For service and maintenance purposes the X-ray examination apparatus can be readily transported to an appropriate site.

It is to be noted that a mobile X-ray examination apparatus, notably a computer tomography apparatus, is known from European Patent Application No. 297 138.

The X-ray examination apparatus and the patient table disclosed in the latter Patent Specification, however, do not have a common, mobile base. As a result, after displacement of the X-ray apparatus, the patient table will have to be accurately positioned with respect to the apparatus prior to the examination.

An embodiment of an X-ray examination apparatus in accordance with the invention is characterized in that the supporting means is pivotably suspended, by way of two pivots, to a two-armed bracket which is rotatably connected to the base by way of a foot, a centre line of which coincides with the swivel axis.

Because of this suspension, the trajectory plane can be tilted with respect to the patient table, thus enabling irradiation of slices other than those extending perpendicularly to the longitudinal direction.

A further embodiment of an X-ray examination apparatus in accordance with the invention is characterized in that the control console is pivotably connected to the patient table and can be positioned against the patient table in the direction substantially parallel to the longitudinal direction, the keyboard and the television monitor being situated over the patient table in the contacting position.

Examination parameters, such as the high voltage for the X-ray source or the start of an irradiation cycle, and adjustment variables concerning the image reconstruction of the absorption distribution can be adjusted via the keyboard which is connected to the control console. The construed absorption distributions can be observed on the television monitor. For radiation shielding use can be made of, for example a window of leaded glass which forms part of the control console. The radiation shielding control console precludes the need for separate radiation shielding means in the examination room. Because of the integrated fit of the control console against the patient table, the control console does not form an obstruction during transport of the X-ray examination apparatus.

A further embodiment of an X-ray examination apparatus in accordance with the invention is characterized in that a first portion of the table top comprises a carriage which is slidable in the longitudinal direction with respect to the base, a second portion of the table top being connected to the first portion so as to be pivotable about a pivot axis which extends perpendicularly to the longitudinal direction and the swivel axis.

The object is displaced in the longitudinal direction with respect to the X-ray source by sliding the carriage. When exposures are made in a stationary state of the X-ray source, a number of substantially contiguous projection images (scanogram) can be obtained by displacing the table intermittently along the X-ray source. Two-dimensional projections of medically interesting details can be observed in the scanogram, so that the position of a relevant image slice in the patient can be determined. For transport of the X-ray examination apparatus, the slide can be displaced to a position which is situated furthest from the trajectory plane, so that the table top can be folded back and the supporting means swivelled with respect to the base.

Figure 1B:
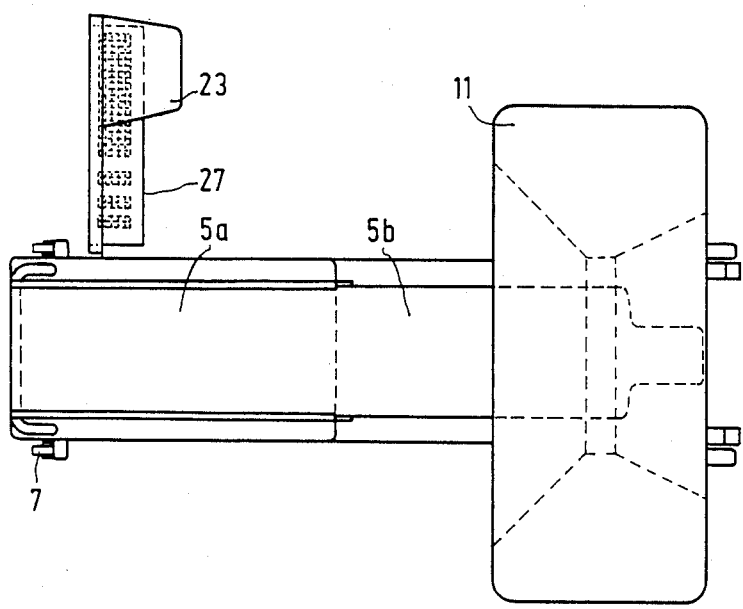
Figure 2:
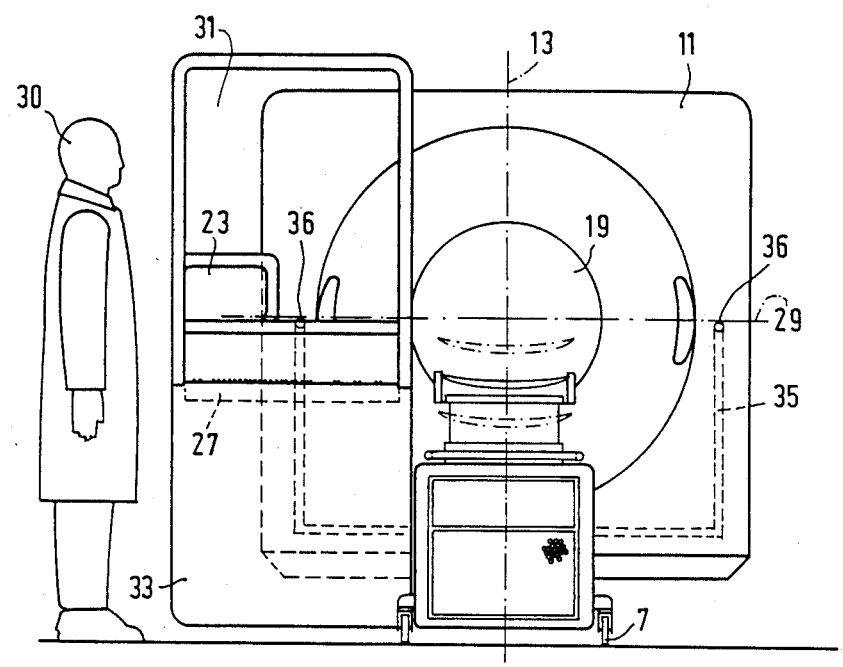
Figure 3:
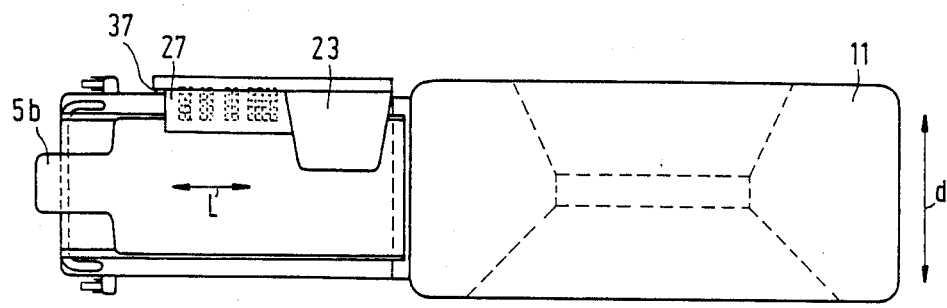

An embodiment of an X-ray examination apparatus in accordance with the invention will be described in detail hereinafter with reference to the accompanying drawing. Therein:

FIGS. 1a and 1b are a side elevation and a plan view, respectively, of the X-ray examination apparatus, in accordance with the invention, FIG. 2 is a front view of the X-ray examination apparatus, and FIG. 3 is a plan view of the X-ray examination apparatus in the transport condition.

FIG. 1a and FIG. 1b show a patient table 1 with a base 3 and a table top 5a, 5b. The base 3 comprises casters 7; for example, one pair of casters at one side is of the swivel-type. On the base 3 there is mounted a carriage 8 which is slidable in a longitudinal direction L and an upper side of which forms a first table top portion 5a. A second table top portion 5b is pivotable about a pivot shaft 9 and can be folded, for example onto the first table top portion 5a. A supporting means 11, a contour of which is only diagrammatically shown in the Figure, is arranged on the base 3 so that its foot 12 can swivel about a swivel axis 13. An X-ray source 15 and a detector array 17 are mounted on the supporting means 11 in a trajectory plane perpendicular to the plane of drawing. The detector array 17 is represented as a succession of detectors arranged along a segment of circle, which succession can rotate about a cavity 19 together with the X-ray source 15; however, use can alternatively be made of a stationary detector array extending along the entire circumference of the circle. The X-ray source 15 is capable of emitting a fan-shaped X-ray beam which is collimated so as to be comparatively narrow in the longitudinal direction L. The attenuated X-rays incident on the detector array 17 after irradiation of a patient (not shown in the Figure) produces a detector current whose value can be stored in a digital image processing unit 21 which is accommodated, for example in the base 3. An absorption distribution of a slice perpendicular to the plane of drawing can be construed by combining the detector signals generated for a number of irradiation directions associated with positions of the X-ray source 15 and the detector array 17 which are situated on a segment of circle, which operation can be carried out in the digital image processing unit 21. This image can be displayed, for example on a monitor 23 which is mounted on a control console 25. Using a keyboard 27 which is also mounted on the control console 25, an image of the absorption distribution in the trajectory plane can be manipulated. Moreover, via the keyboard 27 control signals can be applied to the X-ray source 15 and the detector array 17. The table top can also be displaced in the longitudinal direction L, so that the patient is displaced between the stationary X-ray source 15 and the detector array 17, thus producing a scanogram consisting of a series of contiguous projection images. From the scanogram the position of medically interesting details along a longitudinal axis can be determined, after which the table top can be displaced so that these details are present within the trajectory plane. The supporting means 11 can be tilted through an angle of, for example 20° around an axis 29 which emerges at right angles from the plane of drawing. The trajectory plane can thus be tilted with respect to the base 3. The height of the table top is adjustable in dependence on a position of the supporting means 11. By bringing the supporting blocks 14 in contact with the floor by means of a spindle (not shown in the Figure), the X-ray apparatus can be fixed with respect to the floor.

FIG. 2 is a front view of the X-ray apparatus in the operational condition; it is clearly shown that the width of the supporting means 11 is greater than a distance between the casters 7. The height of the control console 25 is greater than a mean length of a radiologist 30 using the X-ray examination apparatus. An upper portion 31 of the control console 25 is provided with a light-transparent, radiation shielding substance, for example leaded glass. The lower portion 33 of the control console also contains radiation-absorbing material. The keyboard 27 on the control console 25 is arranged at a suitable height for the radiologist 30. The supporting means 11 is suspended to the two-armed bracket 35 in pivots 36 and can be tilted, for example manually around the axis 29.

FIG. 3 shows the X-ray examination apparatus in the transport condition and illustrates how the swivelling of the supporting means 11 about the swivel axis 13 enables the supporting means 11 to be rotated with respect to the base 3 to a position in which the trajectory plane extends parallel to the longitudinal direction L. To this end, the carriage 8 is first moved backwards so far that the table top portion 5b is situated outside the cavity 19, after which the table top portion 5b is folded back onto the table top portion 5a. The supporting means 11 can then be swivelled about the swivel axis 13 until it reaches the position shown in FIG. 3. Because the control console is swivelled back against the base 3, lateral dimensions of the X-ray examination apparatus are small enough for the X-ray examination apparatus to fit, for example between door posts.

What is claimed is:

1. An X-ray examination apparatus having an operating mode and transport mode comprising a patient table defining a longitudinal direction with a mobile base and a supporting means whereto an X-ray source and an array of X-ray detectors are connected, means for rotatably securing the X-ray source for rotation in a trajectory plane around an object to be arranged on the patient table, during which rotation a substantially flat slice of the object is irradiated from different directions, said plane being transverse said direction in said operating mode, X-rays attenuated by the object being detectable by the detectors and an absorption distribution of said slice determined from detector generated signals, said supporting means being secured on the base and swivelled with respect to the base around a swivel axis extending perpendicularly to the base such that said plane extends along said direction in said transport mode.

2. An X-ray examination apparatus as claimed in claim 1, wherein the supporting means is pivotably suspended, by way of two pivots, to a two-armed bracket which is rotatably connected to the base by way of a foot, a centre line of which coincides with the swivel axis.

3. An X-ray examination apparatus as claimed in claim 1 comprising a control console with a keyboard, a television monitor and a radiation shielding section wherein the control console is pivotably connected to the patient table and positioned against the patient table in a direction substantially parallel to the longitudinal direction in said transport mode, the keyboard and the television monitor being situated over the patient table in said operating mode.

4. An X-ray examination apparatus as claimed in any one of the preceding claims, wherein a first portion of the table top comprises a carriage which is slidable in the longitudinal direction with respect to the base, a second portion of the table top being connected to the first portion so as to be pivotable about a pivot axis which extends perpendicularly to the longitudinal direction and the swivel axis.

5. An X-ray examination apparatus as claimed in claim 1 wherein the base is secured on wheels spaced in a direction transverse said longitudinal direction and an external width dimension of the supporting means in a direction perpendicular to the trajectory plane is about the same as that of the spacing of said wheels.

6. An X-ray examination apparatus as claimed in claim 2 comprising a control console with a keyboard, a television monitor and a radiation shielding section wherein the control console is pivotably connected to the patient table and positioned against the patient table in a direction substantially parallel to the longitudinal direction in said transport mode, the keyboard and the television monitor being situated over the patient table in said operating mode.

7. An X-ray examination apparatus as claimed in claim 2 wherein the base is secured on wheels spaced in a direction transverse said longitudinal direction and an external width dimension of the supporting means in a direction perpendicular to the trajectory plane is about the same as that of the spacing of said wheels.

8. An X-ray examination apparatus as claimed in claim 3 wherein the base is secured on wheels spaced in a direction transverse said longitudinal direction and an external width dimension of the supporting means in a direction perpendicular to the trajectory plane is about the same as that of the spacing of said wheels.

9. An X-ray examination apparatus as claimed in claim 4 wherein the base is secured on wheels spaced in a direction transverse said longitudinal direction and an external width dimension of the supporting means in a direction perpendicular to the trajectory plane is about the same as that of the spacing of said wheels.

10. An X-ray examination apparatus comprising:

a base having a length and a width dimension;

a patient table secured to the base having first and second patient carrying portions spaced along said length dimension;

means for rotatably securing the first portion to fold over the second portion in an apparatus transport mode and to extend co-extensive with the first portion along said length dimension in an examination mode;

support means pivotally secured to the base adjacent to the first portion when extended and having a first transport mode and a second examination mode; and X-ray source means and X-ray detector means secured to the support means for rotation about an object in a trajectory plane normal to said length dimension for irradiating the object with a radiation slice, said source means and detector means having a width dimension transverse said plane about the same as said base width dimension and a length dimension parallel to said plane substantially greater than said base width dimension, said support means being arranged so that the plane is transverse said base length dimension in said examination mode and parallel to said base length dimension in said transport mode.

* * * * *